United States Patent [19]

D'Amico et al.

[11] 4,323,686
[45] Apr. 6, 1982

[54] BENZOTHIAZOLEETHANIMIDAMIDES

[75] Inventors: John J. D'Amico, Olivette; John T. Marvel, St. Louis, both of Mo.

[73] Assignee: Monsanto Company, St. Louis, Mo.

[21] Appl. No.: 214,910

[22] Filed: Dec. 10, 1980

Related U.S. Application Data

[62] Division of Ser. No. 68,993, Aug. 23, 1979, Pat. No. 4,283,220.

[51] Int. Cl.³ .................. C07D 277/68; C07D 277/70
[52] U.S. Cl. .................................................. 548/165
[58] Field of Search ........................................ 548/165

[56] References Cited

U.S. PATENT DOCUMENTS

| | | | |
|---|---|---|---|
| 2,947,782 | 8/1960 | Benneville et al. | 260/551 |
| 3,586,691 | 6/1971 | Scott | 260/304 |
| 3,717,690 | 2/1973 | Newman | 260/945 |
| 3,923,491 | 12/1975 | O'Brien et al. | 71/76 |
| 3,989,737 | 11/1976 | Sawaki et al. | 260/472 |
| 4,049,419 | 9/1977 | D'Amico | 71/76 |
| 4,075,216 | 2/1978 | D'Amico | 260/294.8 |

FOREIGN PATENT DOCUMENTS 48-10182  3/1973  Japan .

*Primary Examiner*—Donald G. Daus
*Assistant Examiner*—D. B. Springer
*Attorney, Agent, or Firm*—Stanley M. Tarter; Richard H. Shear; Howard C. Stanley

[57] ABSTRACT

2-Oxo-3-benzothiazoleethanimidamides have been found to be effective in regulating the growth of leguminous plants.

7 Claims, No Drawings

BENZOTHIAZOLEETHANIMIDAMIDES

This is a division of application Ser. No. 68,993 filed Aug. 23, 1979, now U.S. Pat. No. 4,283,220 issued Aug. 11, 1981.

This invention relates to the use of certain benzothiazoleethanimidamides to regulate the growth of leguminous plants. More specifically, it relates to the regulation of leguminous plants, e.g., soybeans, by application of compounds having the formula

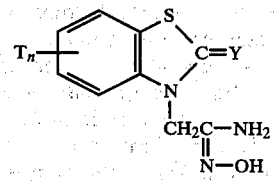

wherein T is halogen or trifluoromethyl, n is 0, 1 or 2 and Y is oxygen or sulfur. Preferred are those compounds in which Y is oxygen, n is 0 or 1 and T is halogen.

The term "halogen" is understood to include chloro, fluoro, bromo and iodo.

The compounds of the foregoing formula may be prepared by reaction of the appropriate substituted acetonitrile and hydroxylamine hydrochloride in a suitable solvent in accordance with the following equation:

Useful solvents include lower alcohols, e.g., those having up to four carbon atoms, tetrahydrofuran, dimethylformamide, dimethylsulfoxide and the like.

Useful bases include ammonium hydroxide, alkali metal carbonates and alkali metal hydroxides, e.g., sodium and potassium hydroxide and tertiary amines.

The method of preparing the acetonitrile precursor is known and has been disclosed in U.S. Pat. Nos. 4,049,419 and 3,993,468. Additionally, copending application Ser. No. 55,144 filed July 5, 1979, entitled "Derivatives Of 2-Thioxo-3-Benzothiazoline Acetonitrile And Their Use As Leguminous Plant Growth Regulants" discloses the preparation of the acetonitrile precursors wherein Y is sulfur. To illustrate the above process for preparing the compounds of the invention the following procedure has been used:

A stirred slurry containing 0.1 mol of the appropriate substituted acetonitrile in 700 to 900 ml of ethyl alcohol was heated to 60° C. and then allowed to cool to room temperature. To this stirred mixture, a solution containing 7 g (0.1 mol) of hydroxylamine hydrochloride in 25 ml of water was added in one portion and stirring continued at 25°–30° C. for six hours. A solution containing 6.4 g (0.06 mol) of potassium carbonate in 25 ml of water was added and stirring continued at 25°–30° C. for 18 hours. After the addition of 500 to 1000 ml of water, stirring was continued at 25°–30° C. for 30 minutes. The solid was collected by filtration, washed with water until neutral and air-dried at 25°–30° C. The data is summarized in Table I.

TABLE I

| Example No. | CP No. | T | Y | m.p. °C. | % Yield | % C Calc'd | % C Found | % H Calc'd | % H Found | % N Calc'd | % N Found | % S Calc'd | % S Found |
|---|---|---|---|---|---|---|---|---|---|---|---|---|---|
| 1 | 83204 | H | O | 202–3[a] | 90 | 48.42 | 48.36 | 4.86 | 4.06 | 18.82 | 18.82 | 14.36 | 14.34 |
| 2 | 83330 | 5-Cl | O | 222–3 | 87 | 41.95 | 41.98 | 3.13 | 3.16 | 16.31 | 16.30 | 12.44 | 12.46 |
| 3 | 83242 | 6-Br | O | 216–7[b] | 80 | 35.78 | 35.75 | 2.67 | 2.68 | 13.91 | 13.91 | 10.61 | 10.65 |
| 4 | 83470 | H | S | 191–2[c] | 86 | 45.17 | 45.19 | 3.79 | 3.83 | 17.56 | 17.52 | 26.80 | 26.77 |

[a]Recrystallization from isopropyl alcohol/DMF (1:1)
[b]Recrystallization from DMF
[c]Recrystallization from ethyl acetate

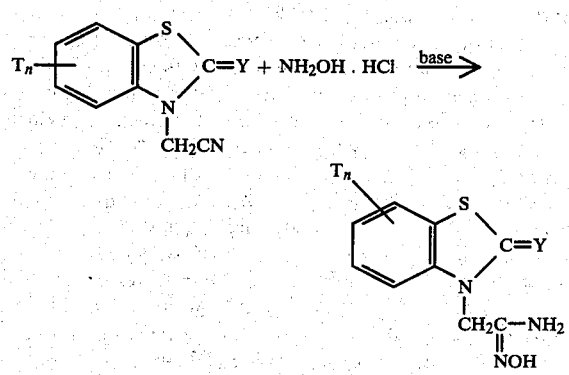

In accordance with the novel aspects of the present invention, the compounds of the foregoing formula are effective plant growth regulants, especially in the regulation of leguminous plants.

The term "plant regulant" or "plant growth regulant," as employed in this application, connotes a material which serves to modify the normal sequential development of a treated plant to agricultural maturity. Such modification may result from the effect of material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, such as an increase or decrease in dry weight accumulation, stature reduction, leaf or canopy alteration, increased branching, terminal inhibition, increased flowering or fruit set.

Modifications in the normal sequential development of a treated plant to agricultural maturity may also be manifested by reduced transpiration or increased carbohydrate deposition or protein content.

It is to be understood that each response may occur in conjunction with other responses, but may occur separately. For example, depending upon various factors realized by those skilled in the art to effect activity, the data illustrated below demonstrates that the compounds of the present invention sometimes alter the leaf morphology even though the plants are not reduced in stature.

The regulation of plants in accordance with the instant invention does not include the total inhibition or the killing of such plants. Although phytotoxic amounts of the materials disclosed herein might be employed to exert a herbicidal (killing) action, it is contemplated herein to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amount will vary, not only with the material selected, but also with the modifying effect desired, the species of plant and its stage of development, the plant growth medium and whether a permanent or transitory effect is sought.

To illustrate the variety of regulatory responses observed, the compounds of the invention were tested in accordance with the following procedure.

A number of soybean plants are grown from seeds in plastic pots in the greenhouse for a period of one week at which time the plants are thinned to one plant per pot. When the second trifoliate leaf is fully expanded, the plants are treated with a solution of the active ingredient in acetone and water. Aqueous Tween 20 is used as a surfactant.

When the fifth trifoliate leaf of the control is fully expanded, the treated plants are compared with the non-treated control plants and the observations recorded.

The following observations were made when soybeans were treated at the indicated rates with the compounds of the foregoing formula.

| Compound of Example No. | Rate (kg/ha) | Observations |
| --- | --- | --- |
| 1 | 0.112 | leaf alteration of new growth, inhibition of dry weight |
|   | 0.56 | leaf alteration of new growth, leaf inhibition |
|   | 2.8 | leaf alteration of old and new growth, leaf inhibition, altered canopy, chlorosis, inhibition of dry weight |
| 2 | 0.112 | inhibition of dry weight |
|   | 0.56 | leaf alteration of new growth, inhibition of dry weight |
|   | 2.8 | leaf alteration of new growth, inhibition of dry weight |
| 4 | 0.112 | none |

-continued

| Compound of Example No. | Rate (kg/ha) | Observations |
| --- | --- | --- |
|   | 0.56 | leaf alteration of new growth, leaf inhibition |
|   | 2.8 | stature reduction, leaf alteration of old and new growth, leaf inhibition |

From the above data, it can be seen that the compounds of the present invention are especially effective in altering the leaf morphology of soybean plants.

Alteration of the leaf morphology of leguminous plants is important because leguminous plants have canopies that effectively inhibit sunlight from reaching the lower leaves. For example, only about 50% of a soybean plant's leaves intercept light for photosynthesis. Approximately 85% of the light is absorbed by the outer layer of leaves. Many researchers feel that by altering the morphology of the leaves such that the canopy is altered, light may fall more deeply into the canopy, and yields could be increased.

Weber, in "Field Crop Abstracts," Volume 21, No. 4, pages 313–317, states that "greater light penetration, resulting in greater amount of the [soybean] plant canopy having a light intensity above 150 f.c., generally led to higher seed yields." Johnson et al, in "Crop Science," Volume 9, pages 577–581, states that "adding light increased the yields of bottom, middle and top canopy positions of [soybean] plants 30, 20 and 2% respectively." Thus, it would be highly beneficial if a method was found whereby the leaves of such plants could be altered such that a greater number of leaves could be illuminated.

In practicing the plant growth regulating methods of this invention, the active ingredient can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent, or emulsifying agent or any suitable combination of these.

When applying the active ingredient to leguminous plants, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful in applying the active ingredient to leguminous plants include, for example, Stoddard solvent, acetone, alcohols, glycols, ethyl acetate, benzene and the like. Such leguminous plant growth regulating compositions, particularly liquids and wettable powders, usually contain as a conditioning agent one or more surface-active agents in amounts sufficient to render a given composition readily dispersible in water or in oil. By the term "surface-active agent," it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Compositions of this invention generally contain from about 5 to 95 parts active ingredient, about 1 to 50 parts surface-active agent and about 4 to 94 parts solvent, all parts being by weight based on the total weight of the composition.

Desirable modification of leguminous plants may be achieved by applying the above-described plant regulants to the plant locus. The term "plant locus" is understood herein to include the plant growing medium, such as the soil, as well as the seeds, emerging seedlings, roots, stems, leaves, flowers, fruits or other plant parts.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. If desired, application of the compositions of the invention to leguminous plants can be accomplished by incorporating the compositions in the soil or other media in the area where modification of the plants is desired.

In selecting the appropriate non-toxic rate of application of the active ingredient to leguminous plants, it will be recognized that precise rates will also be dependent upon the mode of application, such as soil incorporation, band application, pre-plant seed treatment, result desired and various other factors known to those skilled in the art. In applications to the soil habitat of germinant seeds, emerging seedlings, and established vegetation for the regulation of plant growth, the active ingredients are applied in amounts of from about 0.056 to 22.4 kilos/hectare. Foliar application is particularly advantageous and is preferred especially from about 0.112 to about 3.36 kilos/hectare.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

We claim:

1. A compound having the formula

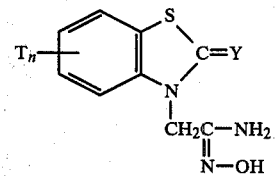

wherein T is halogen or trifluoromethyl, n is 0 or 1 and Y is oxygen or sulfur.

2. A compound according to claim 1 wherein Y is oxygen.

3. A compound according to claim 1 wherein n is 0.

4. A compound according to claim 2 wherein n is 0.

5. A compound according to claim 1 wherein Y is sulfur.

6. A compound according to claim 5 wherein n is 0.

7. A compound according to claim 1 wherein T is halogen and n is 1.

* * * * *